United States Patent [19]

Loeb et al.

[11] Patent Number: 4,525,164
[45] Date of Patent: Jun. 25, 1985

[54] WEARABLE MEDICATION INFUSION SYSTEM WITH ARCUATED RESERVOIR

[75] Inventors: Marvin P. Loeb, Chicago; Arne M. Olson, Villa Park, both of Ill.

[73] Assignee: Biotek, Inc., Santa Ana, Calif.

[21] Appl. No.: 257,002

[22] Filed: Apr. 24, 1981

[51] Int. Cl.³ .............................................. A61M 5/14
[52] U.S. Cl. .................................. 604/131; 604/151; 604/154; 128/DIG. 12; 222/101; 222/326; 222/386
[58] Field of Search ........... 128/213 R, 214 E, 214 F, 128/260, 261, 273, DIG. 12, DIG. 13; 604/131, 132, 151, 153, 154, 155; 222/101, 102, 326, 327, 386

[56] References Cited
U.S. PATENT DOCUMENTS 3,151,616 10/1964 Selfon .............................. 128/214 F
3,198,385 8/1965 Maxwell .......................... 128/214 F
3,384,080 5/1968 Muller ............................. 128/214 F
4,012,177 3/1977 Yakich ........................ 128/214 F X
4,201,207 5/1980 Buckles et al. ................... 128/214 F
4,210,138 7/1980 Jess et al. ....................... 128/214 E
4,313,439 2/1982 Babb et al. ...................... 128/214 F

FOREIGN PATENT DOCUMENTS 2920975 11/1980 Fed. Rep. of Germany ... 128/214 F

Primary Examiner—Lee S. Cohen
Attorney, Agent, or Firm—Dressler, Goldsmith, Shore, Sutker & Milnamow, Ltd.

[57] ABSTRACT

A wearable medicator suitable for controlled subcutaneous dispensing of a liquid medication into a patient. The medicator utilizes a unique arcuate syringe means to provide a small compact medicator that can be easily worn by the patient. The medicator can provide controlled release of insulin for the treatment of diabetes.

28 Claims, 13 Drawing Figures

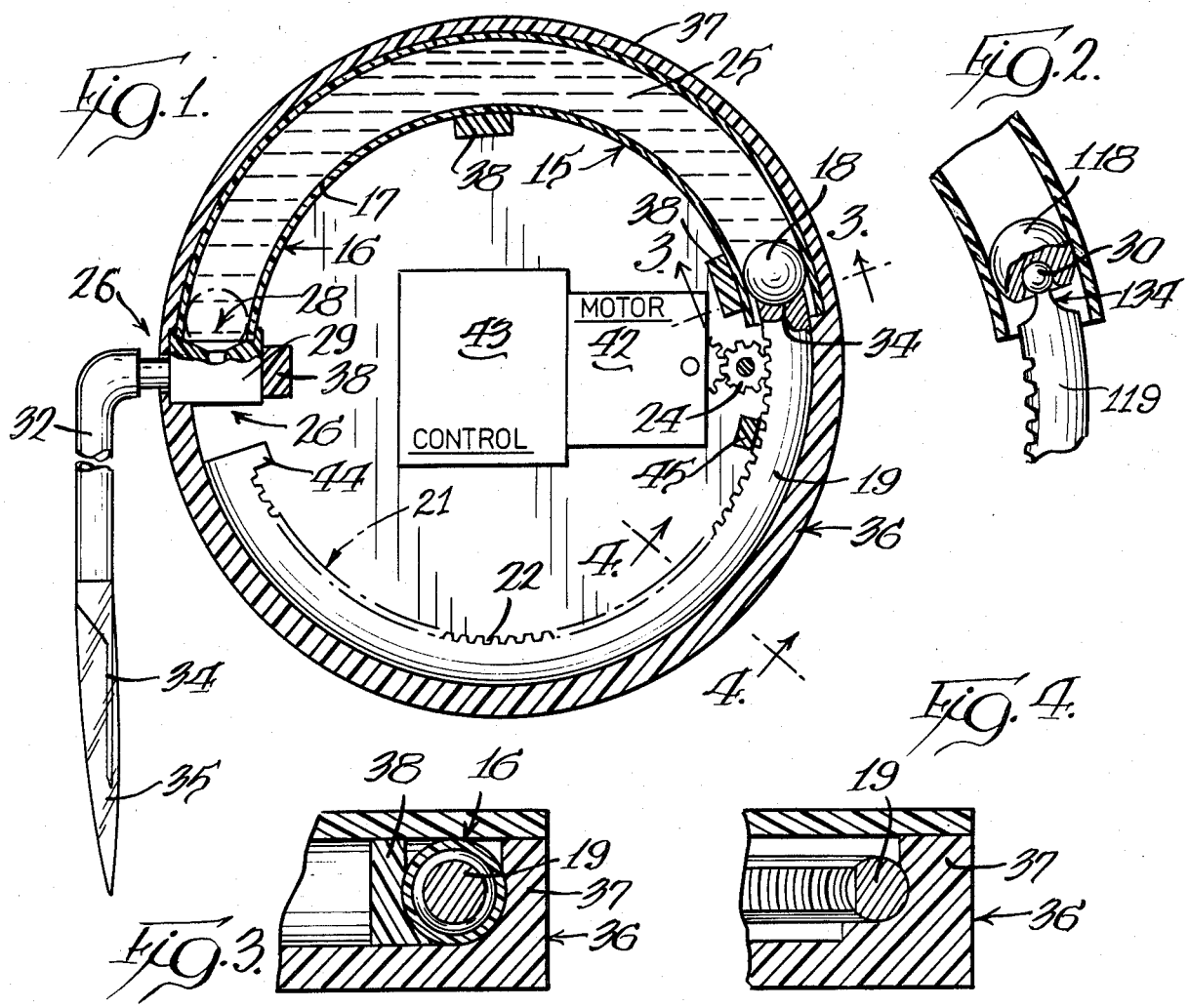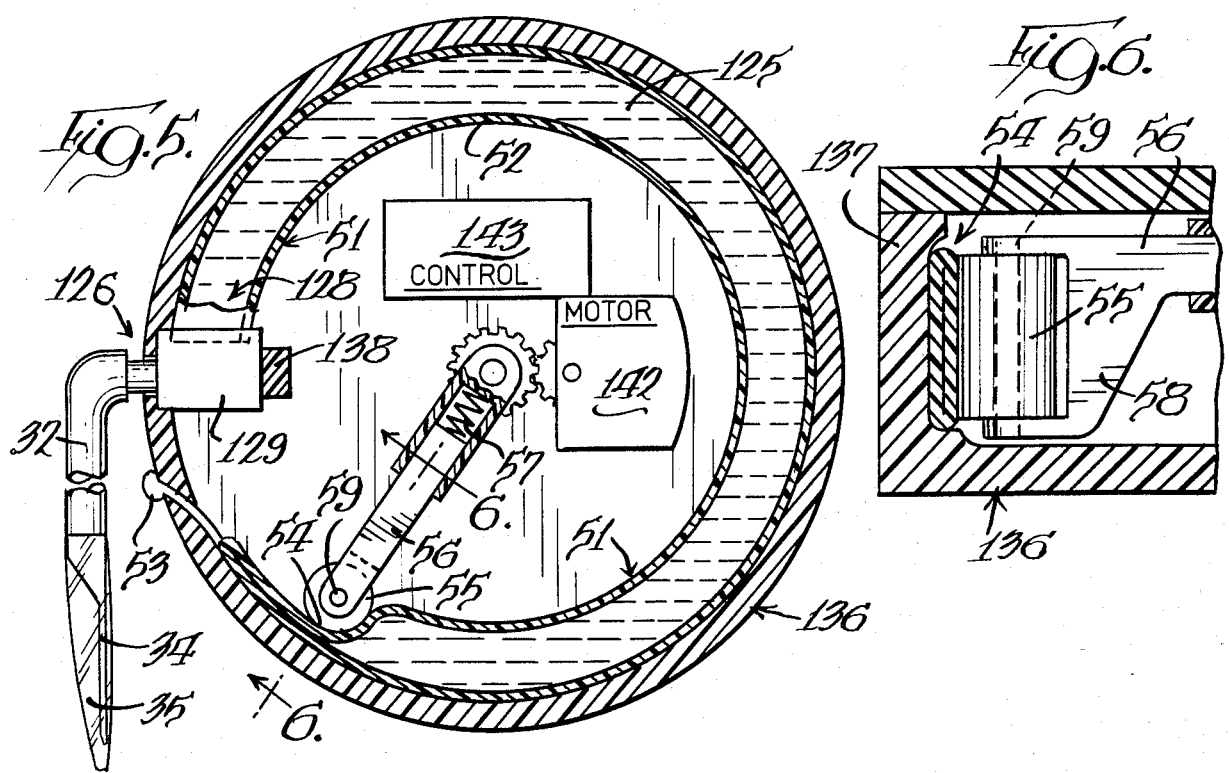

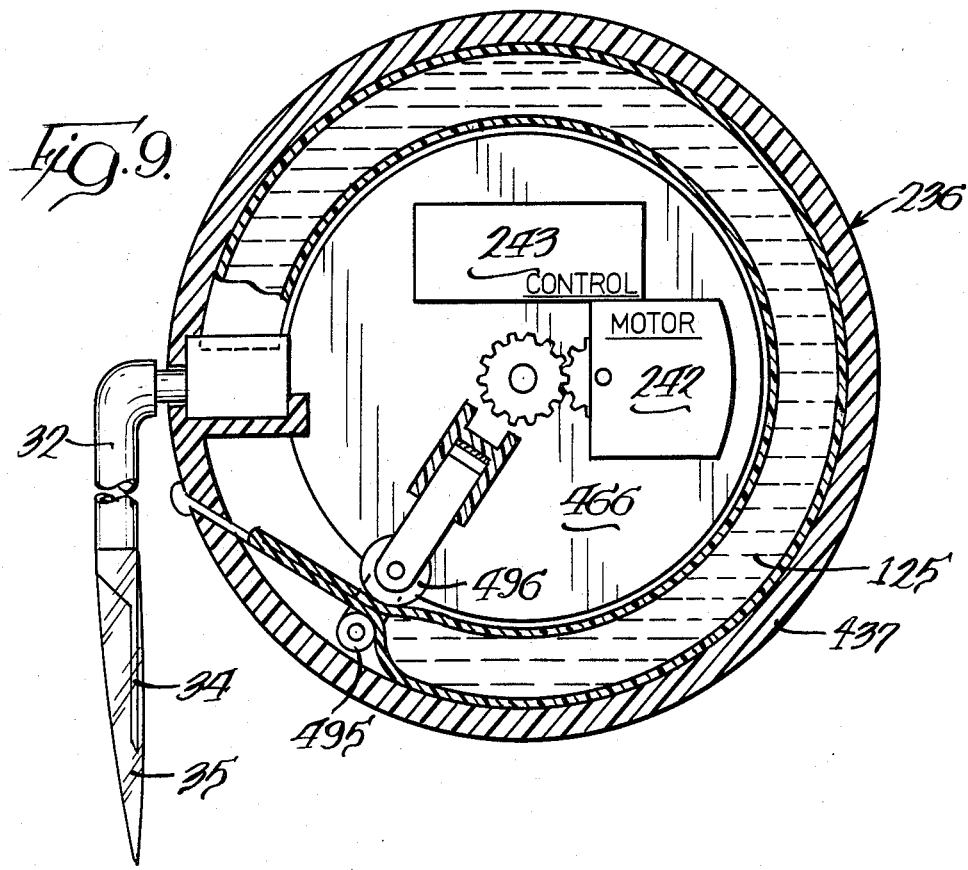
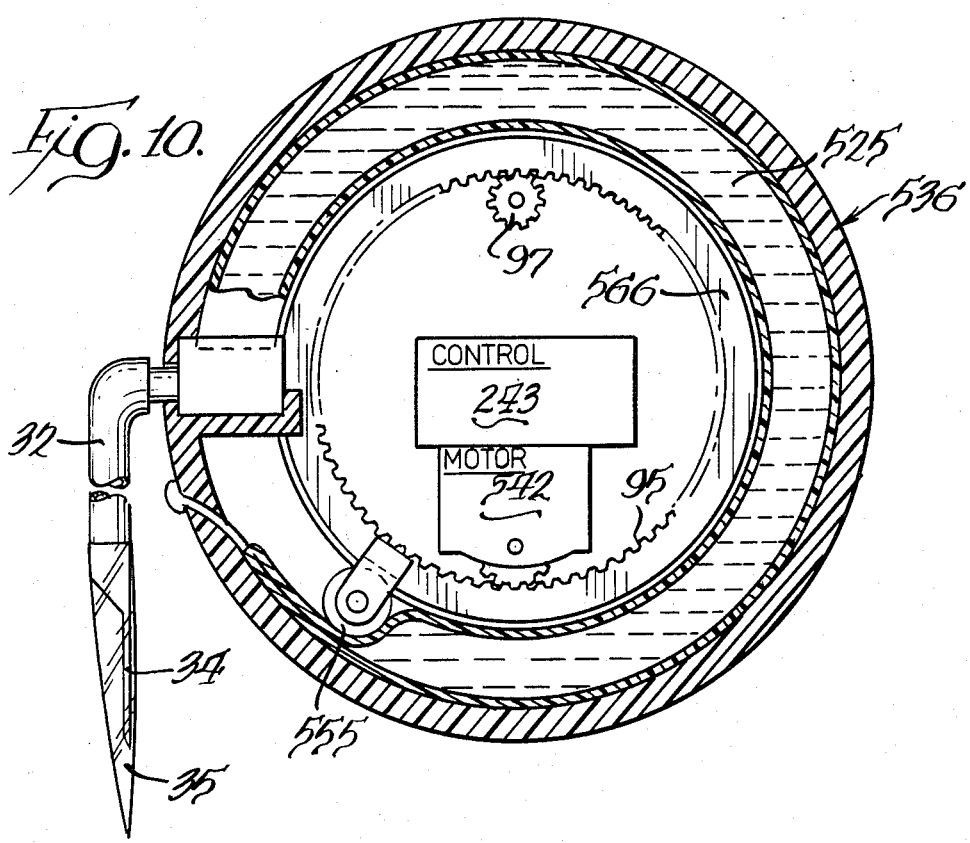

WEARABLE MEDICATION INFUSION SYSTEM WITH ARCUATED RESERVOIR

TECHNICAL FIELD

This invention relates to a system for the administration of a medication, including insulin, to a patient in small, controlled doses over a period of time.

BACKGROUND OF THE INVENTION

There are many medical conditions which require periodic injections of medication. Diabetes, for example, may be controlled by daily, or more frequent, injections of insulin.

Since injection are painful and troublesome, and each injection represents a possibility for infection, the injections are spaced at intervals as far apart as possible, resulting in peak and valley concentrations of the medication in the bloodstream or at the site in the body requiring the medication. This exposes the patient to the possibility of overdose at peak levels and underdose at valley levels.

It has been found in the treatment of certain conditions such as diabetes, more effective treatment results from constant or repeated small doses of medication. An increase in dosage before, during or after meals can help normalize blood glucose levels. This provides improved control of the medical condition and avoids the problems of under and overdone in medication.

Recently, systems have been developed in which a catheter is semi-permanently implanted in a patient, and a liquid medication is supplied to the patient through the catheter from a reservoir. These devices, however, tend to be large and bulky and in some cases require a considerable power source. The devices using conventional syringes are large because of the space needed to operate a linear syringe. Because of their size, many of these devices are designed to be worn on the chest, in a case slung over the user's shoulder, or on a belt around the user's waist.

Accordingly, there is need for a wearable system for effective administration of medication at a reasonable cost. The present invention satisfies that need.

SUMMARY OF THE INVENTION

The present invention utilizes a unique arcuate syringe to provide a small, compact medicator suitable for dispensing insulin or other liquid medication. The arcuate syringe, because of its compact design, will allow for the injection of medication under circumstances where use of a linear syringe would be difficult or impractical. Such an arcuate syringe can also be used to provide a medicator which may be conveniently worn by the patient, e.g. on his wrist.

In one preferred embodiment the syringe comprises an arcuate rigid barrel which can be filled with liquid medication and an arcuate plunger engaged with the barrel to inject the liquid medication into a patient. The arcuate syringe can be removably mounted on a wearable frame. Included in the present system are a motor means to drive the plunger into the barrel and a control means to regulate the amount dispensed. The plunger utilizes a unique piston that cooperates with the barrel as the medication is dispensed. The piston is spheroidal and can move within the barrel relative to the plunger stem to avoid binding with the inside surface of the barrel. This not only aids in the reliability of the medicator but, because of the structure of the syringe, provides a compact system for the accurate metering of liquid medication.

In another preferred embodiment, the syringe comprises a collapsible tubular reservoir removably mounted on the frame. Also mounted on the frame is a displacement assembly to progressively collapse the reservoir and displace the medication out of the reservoir and into the patient.

Yet another embodiment has a resilient tubular reservoir connected to a supply envelope. As the displacement assembly displaces the liquid out of one part of the tubular reservoir, the remainder of the tubular reservoir is refilled with liquid medication from the supply envelope. This increases the total supply of liquid medication available before the reservoir has to be replaced.

Such a medicator can serve several other purposes in addition to dispensing insulin. For example, it can be used to give an emergency injection, such as an antidote to nerve gas poisoning. In such an embodiment a soldier wears the medicator on his wrist and in the event of poisoning presses a button to release the contents of the medicator into his body. Unlike present devices for this purpose which are not mountable on the body, this medicator is easier to use by one exposed to nerve gas poisoning or like situation where time is of the essence.

Instead of "one shot" injection the medicator of the present invention can be set to allow injection of medication over a period of time. Such an injection process avoids the peaks and valleys of single injections and aids in maintaining a nearly constant concentration of certain drugs or hormones in the patient. Such drugs include those used for chemotherapy of cancer and heparin for thromboembolism treatment. The hormone treatments can include injections of thyroid hormones and insulin.

The compact medicator of the present invention is particularly well suited for controlled release of insulin in treating the symptoms of diabetes. Either a continuous slow injection or a series of small injections over a period of time can be provided to avoid the problems of over- and under-medication. Thus, the diabetic patient can be provided with a lightweight wearable unit which includes a readily accessible source of insulin that can be easily refilled or replaced.

Numerous other advantages and features of the present invention will become readily apparent from the claims, drawings and the detailed description of the invention.

BRIEF DESCRIPTION OF THE DRAWINGS

In the accompanying drawings forming part of the application:

FIG. 1 is a plan view of a medicator embodying the present invention with portions broken away to show interior detail and showing an arcuate syringe mounted on a wearable frame and having a spheroidal piston, a stem for moving the piston and a barrel for containing liquid medication;

FIG. 2 is a fragmentary cross-sectional view showing an alternative type of piston mounted on the end of the stem;

FIG. 3 is an enlarged cross-sectional view of the syringe mounted on the frame taken along plane 3—3 of FIG. 1;

FIG. 4 is an enlarged cross-sectional view of the stem as it rests on the frame taken along the plane 4—4 of FIG. 1;

FIG. 5 is a plan view, partly in section and showing a medicator of the present invention which includes a collapsible tubular reservoir, motor means and control means mounted on a frame;

FIG. 6 is an enlarged cross-sectional view taken along plane 6—6 of FIG. 5 showing a medication displacement assembly which includes a roller collapsing the tubular reservoir against a wall of the frame;

FIG. 9 is a plan view similar to FIG. 7 except showing two rollers cooperating to collapse the tubular reservoir;

FIG. 10 is a plan view similar to FIG. 7 except showing an annular rotation plate on which the roller is mounted and with the control means and motor means being mounted on the base;

DESCRIPTION OF THE PREFERRED EMBODIMENTS

Figure 7:
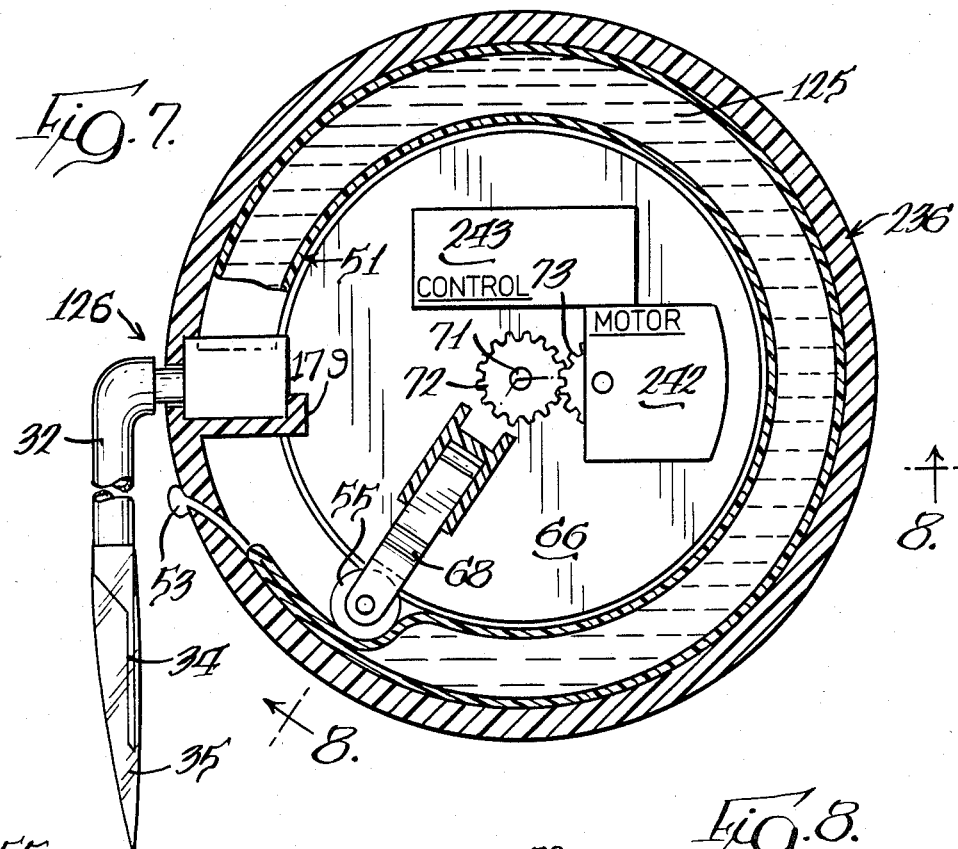
FIG. 7 is a plan view similar to FIG. 5 except showing a displacement assembly which includes a rotation plane onto which the control means, motor means and roller are mounted.

While this invention is susceptible to embodiment in different forms, there are shown in the drawings and will herein be described in detail preferred embodiments of the invention. It should be understood, however, that the present disclosure is to be considered as an exemplification of the principles of the invention and is not intended to limit the invention to the embodiments illustrated.

The precise shapes and sizes of the components herein described are not essential to the invention unless otherwise indicated. For ease of description, the medicator of this invention will be described in a normal operating position and such terms as up, down, top, bottom, etc. will be used with reference to this position. It will be understood, however, that the medicator of this invention may be manufactured, stored, transported, used and sold in an orientation other than the position described.

The medicator of this invention utilizes certain conventional motor means and control means, the details of which, though not fully illustrated or described, will be apparent to those having skill in the art and an understanding of the necessary functions to such mechanisms. The choice of materials is dependent on the particular application involved and other variables as those in this skill of art will appreciate.

Referring now to the drawings, FIG. 1 shows a preferred embodiment of an arcuate syringe mounted on a wearable frame. The arcuate syringe 15 comprises an arcuate barrel 16 of substantially uniform cross section defining a liquid reservoir with a wall portion 17, a piston 18 slidably and sealingly received within the barrel and a stem 19 having an arcuate shape adapted to be received within the arcuate barrel 16.

Lateral surface 21 of the stem 19 is provided with a rack 22 for engaging a drive means such as a spindle or pinion 24. As the pinion 24 is rotated, the stem 19 is driven into the barrel 16 moving the piston 18 along the barrel to displace a liquid medication 25 within the barrel.

The opposite end of the barrel forms a dispensing nozzle 28 which is joined to a connector means 26 to introduce the medication 25 into the patient. The connector means 26 comprises a connector 29 attached to the nozzle 28 and a segment of flexible tubing 32 attached between the connector and a needle 34 which is inserted in the patient. The needle 34 is provided with a needle cover 35 for use during shipment and storage.

Two suitable configurations for a piston are illustrated in FIGS. 1 and 2. FIG. 1 shows a resilient spheroidal piston 18 which is slidably contacted by a cupped distal end 34 of the stem 19. The spheroid shape of the piston 18 allows it to rotate within the barrel 16 on the cupped distal end 34 of the stem 19 without binding. This adds to the reliability of the medicator and aids in the accurate metering of the medication 25.

The second embodiment of FIG. 2 shows the distal end 134 of the stem 119 having a knob 30 which fits inside a resilient spheroidal piston 118. As the piston 118 moves along the barrel 16 it can flex on the knob 30 to avoid binding within the barrel. This increases medicator reliability and accuracy of metering. The piston can be resilient in conjunction with a rigid barrel 16 to obtain a seal or alternatively the piston can be ridged and the barrel substantially rigid such that it has some resiliency to maintain a seal.

The arcuate syringe 15 is removably mounted on a wearable frame 36 which has an upstanding peripheral wall 37. Holding clips 38 affixed to the frame 36 retain the barrel 16 on the frame 36. A motor means such as a spring or electrically driven motor 42 is mounted on the frame to rotate the pinion 24 to drive the stem rack 22. A control means 43 is provided to regulate the motor 42 and the amount and rate of medication dispensed.

A stop 45 on frame 36 engages the shoulder 44 of the stem 19 to stop further movement of the stem after it is fully inserted in the barrel 16. If desired, the stop 45 may be operably connected to the control means 43 e.g. by means of a microswitch, to de-energize the motor 43 after full insertion and indicate to the wearer that the medicator is empty.

The control means 43 and motor 42 can be chosen and set to provide injections of the medication 25 at predetermined intervals or at a constant rate. Because the volume per unit length of the barrel 16 is known, the amount of medication 25 injected into the patient for each given movement by the motor 42 is known. Thus it is possible to accurately meter the amount of medication a patient is given.

The cross-sections of the frame shown in FIG. 1 can best be seen in FIGS. 3 and 4. FIG. 3 shows a cross-section of the barrel 16 as it is retained between the frame wall 37 and the holding clip 38. The holding clip 38 can be made of a resilient plastic material which allows the barrel to be removed and replaced from the frame 36. The holding clip 38 can be part of the frame 36 or separately produced. Also known in FIG. 3 is the stem 19 as it is positioned within the barrel 16.

FIG. 4 shows a cross-section of the frame 36 in those areas where the stem 19 is outside the barrel 16. As can be seen, the stem 19 is positioned against the frame wall 37 restraining the stem from moving up or down. As the rack 22 of the stem 19 engages the pinion 24 (FIG. 1), the frame wall 37 maintains the pinion 24 and rack 22 in mesh.

For use by the patient the syringe 15 would be separable from the frane 36. The piston 18, barrel 16, connector means 29, tube 32, needle 34 and needle cover 35 would be shipped as a sterile integral unit. The patient then mounts the syringe on the frame, swabs a skin injection site with alcohol and removes the needle cover. The control means 43 is then activated to energize the motor 42 to rotate the pinion 24. As the pinion 24 rotates it drives the stem 19 to move the piston 18 along the barrel 16 displacing the medication 25 out of the barrel through the connecting means 26 and into the patient. After a drop of medication appears at the needle end, the patient inserts the needle into his body. This helps to avoid injection of air into the patient.

Another preferred embodiment is shown in FIGS. 5 and 6 wherein the syringe comprises an arcuate collapsible tubular reservoir 51 having walls 52 containing the liquid medication 125. The tubular reservoir 51 is collapsed at a region of contact 54 by a roller 55 rotatably mounted on an arm 56 and roller brace 58. The arm 56 includes a biasing means 57 such as a spring or resilient plastic plug or rod. As the motor 142 rotates the arm 56, the roller 55 contacts and collapses the tubular reservoir 51 pressing its walls 52 together, displacing the medication 125 in the direction of roller movement through the connector means 126 and into the patient. The tubular reservoir 51 is held on the frame 136 by a holding clip 138 and a tab 53. The holding clip 138 also serves as a stop to prevent rotation of the roller 55 and arm 56 after the tubular reservoir 51 has been emptied. If desired, the holding clip 138 may be operably connected by a microswitch or the like to the control means 143 to deactivate the motor 142 after the tubular reservoir 51 has been emptied and indicate such to the wearer. The connector means 126 comprises a connector 129, flexible tube 32, and needle 34, all in fluid communication with the reservoir nozzle 128.

The compressed configuration of the tubular reservoir 51 can be seen in FIG. 6. The tubular reservoir 51 is compressed between the roller 55 and the frame wall 137. The roller is mounted on an axle 59 which is connected to the arm 56 and roller brace 58.

Figure 8:
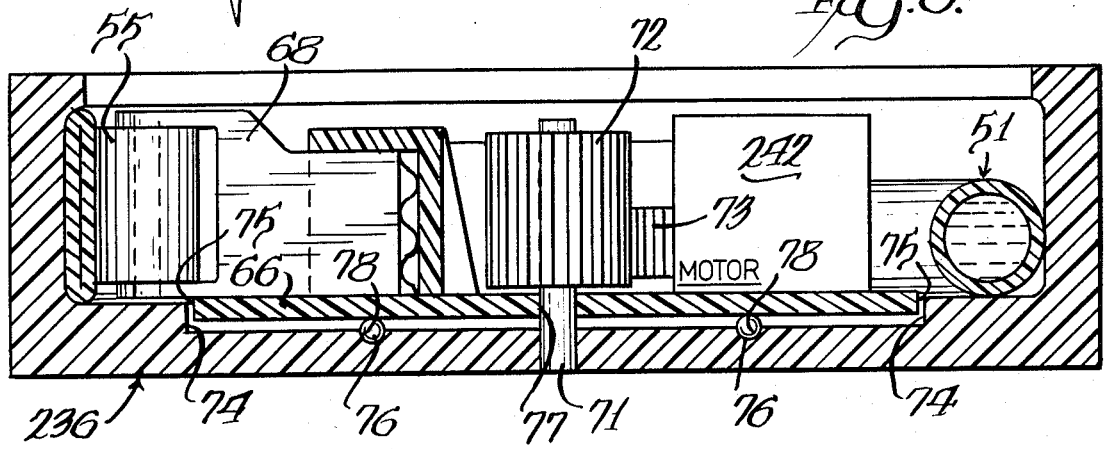
FIG. 8 is an enlarged cross-sectional view taken along plane 8—8 of FIG. 7 showing the rotation plate, and the roller, control means and motor means mounted thereon.

A similar preferred embodiment is set forth in FIGS. 7 and 8. This particular embodiment utilizes a rotation plate 66 on which the motor 242, control means 243, and roller 55 are mounted. Also mounted on the rotation plate is a biased brace 68, which rotatably holds the roller against the tubular reservoir 51. As the rotation plate 66 is rotated by the motor 242 those members mounted on the rotation plate also rotate relative to the frame 236. A spur gear 72 is mounted on a spur gear shaft 71 which is affixed to and does not rotate in relation to the frame 236. The motor 242 has a drive gear 73 which engages the spur gear 72 to turn the rotation plate 66 with respect to the frame.

The frame 236 has a shoulder 74 which retains and aligns the rotation plate along a bearing surface 75 on a rotation plate. The rotation plate 66 is also aligned by a second bearing surface 77 on the rotation plate which is in slidable contact with the spur gear shaft 71. The rotation plate 66 rotates on ball bearings 76 held in place in a groove 78 in the frame 236. These features provide for free turning of the rotation plate 66. The tubular reservoir 51 is held on the frame 236 by means of a holder 179 and tab 53.

The embodiment shown in FIGS. 7 and 8 has the particular advantage of providing a means to hold the roller 55 with a minimum amount of space. Although not illustrated, it is also possible that the shoulder 74 may be geared and the motor drive gear engage this gear to turn the rotation plate. If desired, the motor means 242 may also include a spring-driven mechanism mounted either above or below the rotation plate and operably associated to drive the rotation plate in whole or in part. In such a case, spur gear 72 can serve as part of a dispensing control device.

A similar embodiment is set forth in FIG. 9. In this particular embodiment two rollers 495 and 496 are mounted on the rotation plate 466 to squeeze the tubular reservoir 51 between them. Preferably roller 495 is smaller than roller 496 to save space and avoid moving the reservoir 125 away from the frame wall 437. Another similar embodiment is shown in FIG. 10 wherein the rotation plate comprises an annular disc 566 with an interior geared surface 95 which cooperates with the motor 542 mounted on the frame 536 to move the roller 555 along the tubular reservoir 525. Idler gear 97 mounted on frame 536 helps to retain the annular disc 566 in place.

In the embodiments of FIGS. 5–10, the reservoir 51, connector 129, flexible tube 32, needle 34 and needle cover 35 would be shipped as a sterile integral unit. The patient would then mount the unit on the frame, swab a skin injection site with alcohol, and remove the needle cover 35. The control means is then activated to energize the motor to move the roller or rollers along the length of the tubular reservoir 51. As the roller or rollers move, the tubular reservoir 51 is collapsed, displacing the medication 125 out of the reservoir through the connecting means 126 to the needle 34. After a drop of medication appears at the needle end, the patient inserts the needle into his body.

Figure 11:
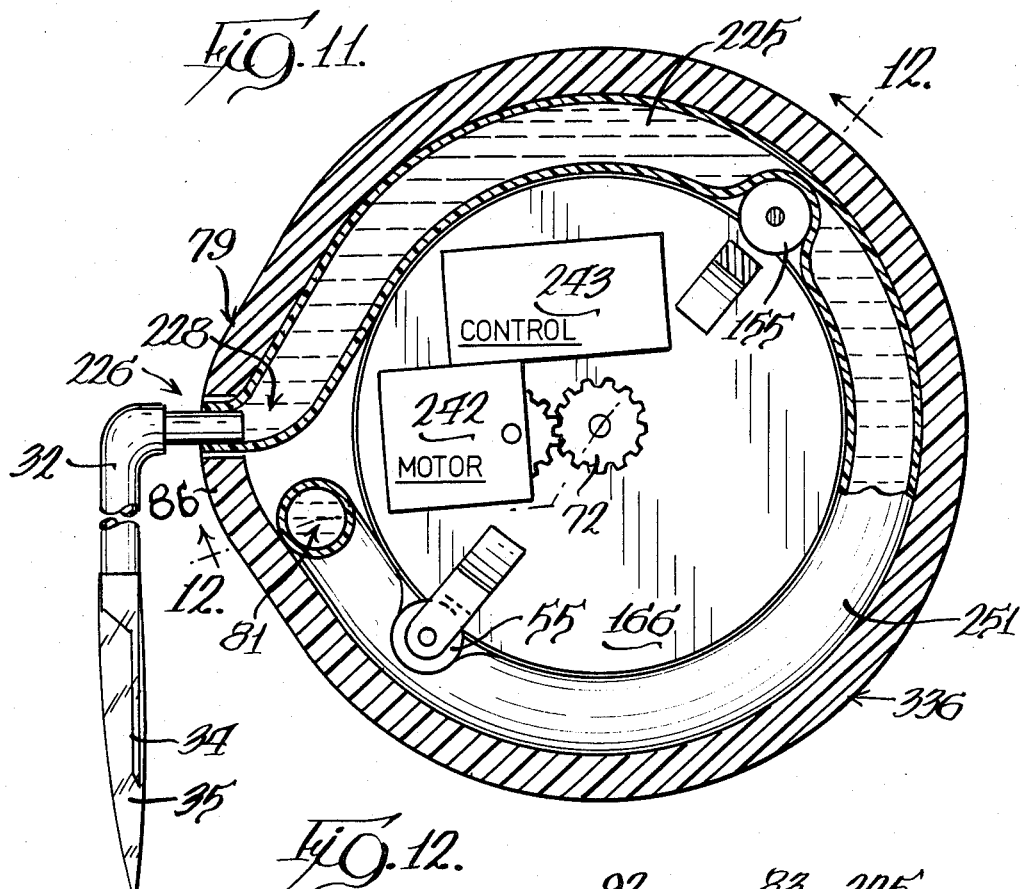
FIG. 11 is a sectional plan view taken along plane 11—11 in FIG. 12 of another medicator embodying the present invention in which the medicator includes a reservoir in fluid communication with a supply envelope and utilizes a pair of rollers to dispense the medication and to withdraw medication from the supply envelope to the reservoir.
Figure 12:
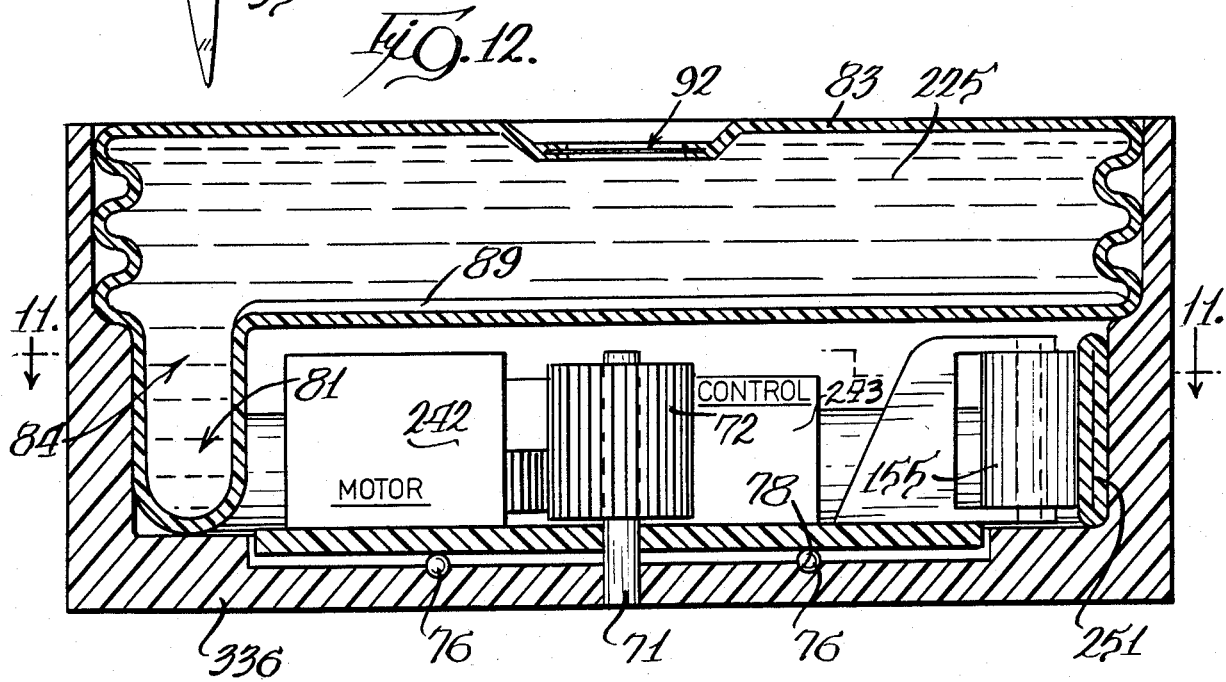
FIG. 12 is an enlarged cross-sectional view taken along the planes 12—12 of FIG. 11 showing a similar arrangement to that of FIG. 8 except showing a reservoir that is in fluid communication with the supply envelope.

A preferred embodiment allowing for increased liquid medication capacity before requiring replacement is shown in FIGS. 11 and 12. FIG. 11 is substantially like FIG. 7 except two rollers 55 and 155 are mounted on the rotation plate 166, the connector means 226 has been modified to allow continuous rotation, and the frame 336 has been provided with a small platform 79 jutting out from the main part of the frame. These modifications allow the rotation plate 166 and the rollers 55, 155 to make several continuous rotations. As before, the roller collapses the tubular reservoir 251 displacing the medication 225 out through the connecting means 226 and into the patient.

However, unlike the previous embodiments, the tubular reservoir 251 does not remain collapsed. The end opposite the nozzle 228 is an inlet 81 for the tubular reservoir 51. As can be seen in FIG. 12, above the tubular reservoir 251 is a collapsible supply envelope 83 which contains medication. Near the edge of the supply envelope 83 is an outlet 84 in fluid communication with the inlet 81 of the tubular reservoir 251. Thus, after a roller has collapsed a section of the tubular reservoir 251, the tubular reservoir being resilient re-expands drawing in medication 225 from the supply envelope 83.

Two rollers are provided to insure a continuous metering of the liquid medication 225 as one of the rollers passes between the connecting means 226 and the inlet of the reservoir 251. The connecting means 226 and the adjacent wall 86 allow one roller to pass over this region of the reservoir without collapsing it thereby permitting the other roller to handle the metering and displacement of the medication 225.

The supply envelope has tapered ridges 89 which may be molded into the surface of the supply envelope 83 to insure that as long as liquid remains within a supply envelope it will be able to drain toward the outlet 84 and thus into the reservoir. When empty, the supply envelope 83 and tubular reservoir 251 can be discarded. Alternatively, to enable refilling of the supply envelope, septum 92 is positioned on the top surface of supply envelope 83 and allows the supply envelope to be refilled externally by means of a hypodermic needle and syringe (not illustrated). Thus, it is possible to refill the medicator without removing the supply envelope and reservoir from the frame.

For use by the patient the reservoir 251, supply envelope 83, connector 226, flexible tube 32, needle 34 and needle cover 35 would be shipped as a sterile integral unit. The patient would then mount the unit as described before. The control means 243 is then activated to energize the motor 242 to rotate the rotation plate 66 and moves the rollers along the reservoir 151. As medication 225 is displaced out of the reservoir 251 and into the patient, more medication enters the reservoir from the supply envelope 83.

Figure 13:
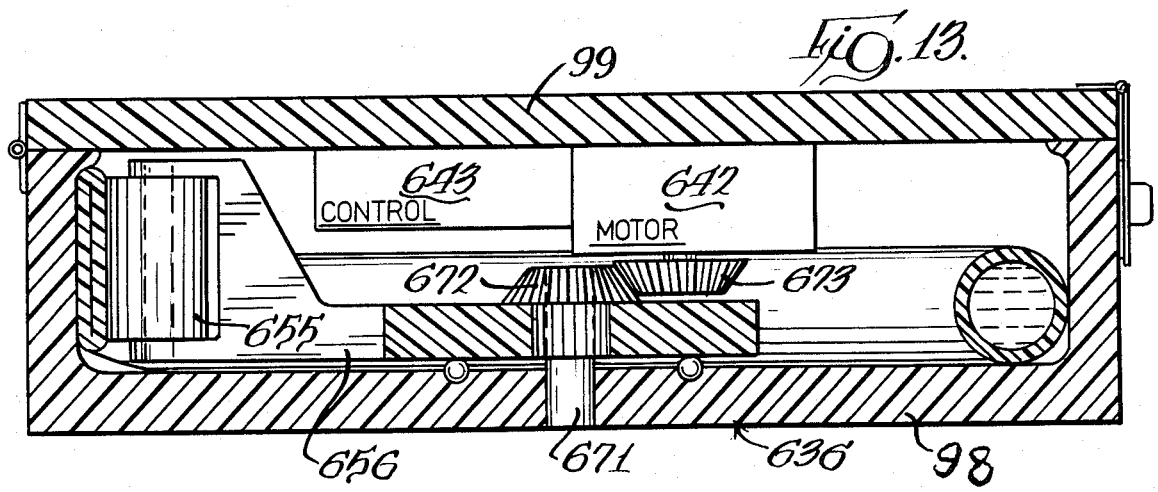
FIG. 13 is a cross-sectional view similar to FIG. 6 but showing the frame comprised of a base member and a cover member on which the control and motor means are mounted.

As shown in FIG. 13, the frame 636 may also be articulated, i.e., constituted by a base member 98 and a cover member 99. The control means 643 and motor means 642 are mounted on the cover member 99 and when the cover member is in a closed position as shown in FIG. 13, motor gear 673 engages gear 672 which is mounted on shaft 671 to turn the arm 656 and thus move the roller 655. Shaft 671 is rotatably mounted on base member 98.

There are several other possible modifications within the scope of the invention. Some of these are discussed above. Others include the use of a fibrous porous cuff around an implantable catheter to allow longer term connection to the body. The dispensing nozzle of the reservoir in such a case is fitted with a sealing membrane or septum which seals the reservoir until it is attached to a connecting means mounted on the frame and having a needle to puncture the sealing membrane.

The foregoing specification is intended as illustrative and is not to be taken as limiting. Still other variations within the spirit and scope of this invention are possible and will readily present themselves to those skilled in the art.

We claim:

1. A wearable medicator suitable for controlled subcutaneous dispensing of liquid medication into a patient which comprises:
    (a) a frame adapted for removable attachment to the patient;
    (b) an arcuate tubular reservoir for liquid medication removably mounted on the frame, the reservoir having a dispensing nozzle and a closed opposite end having means for mounting on the frame;
    (c) a connecting means attached to the dispensing nozzle for introducing the liquid medication into the patient;
    (d) a volume reducing means operably associated with the reservoir so as to dispense the liquid medication from the reservoir;
    (e) motor means operably associated with the volume reducing means, the motor means being surrounded by the tubular reservoir; and
    (f) control means operably associated with the motor means for controlling the action of the volume reducing means.

2. The medicator of claim 1 wherein the motor means is electrically driven.

3. The medicator of claim 1 wherein the motor means and the control means comprise a spring driven clock mechanism.

4. The medicator of claim 1 wherein the arcuate tubular reservoir is substantially rigid.

5. A wearable medicator suitable for controlled subcutaneous dispensing of a liquid medication into a patient which comprises:
    (a) a frame adapted for removable attachment to a patient;
    (b) an arcuate collapsible tubular reservoir for the liquid medication removably mounted on the frame, the reservoir having a dispensing nozzle and a closed opposite end and means for mounting the closed opposite end on the frame;
    (c) a connector means attached to the dispensing nozzle for introducing the liquid medication into the patient;
    (d) a displacement assembly rotatably mounted on the frame in contact with and collapsing the reservoir to displace the liquid medication toward the dispensing nozzle, through the connector means and into the patient;
    (e) motor means mounted on the frame and surrounded by the reservoir to rotate the displacement assembly; and
    (f) control means operably associated with the motor means for controlling the operation of the displacement assembly.

6. The medicator of claim 5 wherein the displacement assembly comprises a roller rotatably mounted on an annular disc with an interior geared surface which cooperates with the control means and motor means mounted on the frame to collapse the reservoir as the disc turns.

7. The medicator of claim 5 wherein the displacement assembly comprises an arm having one end connected so as to be rotated by the motor means and an opposite end, and a roller positioned to contact and collapse the reservoir and rotatably mounted on the opposite end.

8. The medicator in accordance with claim 7 wherein the arm is provided with a biasing means to maintain the roller in contact with the reservoir.

9. The medicator of claim 5 wherein the displacement assembly comprises a rotation plate rotatably mounted on the frame, the control means and motor means are mounted on the plate, a roller is rotatably mounted on the plate in a position so that the roller contacts and collapses the reservoir as the rotation plate turns, and the motor means is operably associated with the frame so as to turn the rotation plate.

10. The medicator of claim 9 wherein the roller cooperates with a second roller also mounted on the rotation plate to squeeze the tubular reservoir between the two rollers to collapse the reservoir.

11. The medicator of claim 10 wherein one roller is smaller in diameter than the other roller.

12. The medicator of claim 5 wherein the frame comprises a base member associated with a cover member, the control means and motor means being mounted on the cover member and operably associated with the displacement assembly when the cover member is in a closed position.

13. The medicator of claim 5 wherein the tubular reservoir has a substantially elliptical cross-section.

14. The medication of claim 5 wherein the means for mounting the closed end is a tab.

15. A wearable medicator suitable for controlled subcutaneous dispensing of liquid medication into a patient which comprises:
(a) a frame adapted for removable attachment to a patient;
(b) a substantially rigid arcuate barrel for containing a supply of the liquid medication removably mounted on the frame, the barrel having an open end and an opposite end terminating in a dispensing nozzle;
(c) a piston slidably and sealingly received within the barrel;
(d) an elongated stem extending from the barrel and having one end in contact with the piston for moving the piston along the barrel, a side, and an arcuate shape permitting the stem to be received within the barrel; the stem together with the piston comprising a plunger;
(e) a connector means attached to the dispensing nozzle for introducing the liquid medication into the patient;
(f) a rotatable spindle mounted on the frame, the spindle engaging the stem to drive the stem into the barrel so as to move the piston along the barrel;
(g) motor means to rotate the spindle; and
(h) control means associated with the motor means to control the operation of the plunger.

16. The medicator of claim 15 wherein the side of the stem is provided with a rack and a pinion is mounted on the spindle, the pinion engaging the rack to drive the stem.

17. The medicator of claim 15 wherein the piston is resiliently and has a generally spherical shape.

18. The medicator of claim 15 wherein the piston is rotatably contacted by the stem.

19. An arcuate syringe comprising:
(a) an arcuate barrel defining a liquid reservoir and having a wall portion, an open end, and an opposite end terminating in a dispensing nozzle;
(b) a piston slidably and sealingly received within the open end of the barrel; and
(c) a stem extending from the open end of the barrel and associated with the piston for moving the piston along the barrel, the stem having an arcuate shape permitting the stem to be received within the barrel.

20. The arcuate syringe of claim 19 wherein the piston has a curved lateral surface with a radius of curvature that is smaller than the radius of curvature of the inner surface of the wall portion, the lateral surface providing substantially line contact with inner surface of the wall portion around the periphery thereof.

21. The arcuate syringe of claim 19 wherein the stem has a lateral surface provided with a rack for engaging a drive means.

22. The arcuate syringe of claim 19 wherein the piston is spheroidal.

23. A liquid medication reservoir for use in a wearable medicator, the reservoir comprising:
(a) an arcuate collapsible tubular reservoir having a dispensing nozzle and a closed opposite end;
(b) a tab on the closed opposite end and adapted to be held by the wearable medicator and;
(c) connector means attached to the dispensing nozzle for introducing liquid medication into a patient.

24. The reservoir of claim 23 wherein the connector means comprises a connector attached to the dispensing nozzle, a needle to be inserted into the patient, and a segment of flexible tubing attached between the connector and the needle.

25. A liquid medication reservoir for a wearable medicator, the reservoir comprising:
(a) a substantially rigid arcuate barrel of substantially uniform cross section having an open end and an opposite end terminating in a dispensing nozzle;
(b) a piston slidably received within the barrel adjacent the open end; and
(c) a connector means attached to the dispensing nozzle for introducing liquid medication into a patient.

26. The reservoir of claim 25 wherein the connector means comprises a connector attached to the dispensing nozzle, a needle to be inserted into the patient and a segment of flexible tubing attached between the connector and the needle.

27. The reservoir of claim 25 wherein the piston is resilient and has a generally spherical shape.

28. A wearable medicator suitable for controlled subcutaneous of a liquid medication into a patient which comprises:
(a) a frame adapted for removable attachment to a patient;
(b) an arcuate collapsible tubular reservoir for the liquid medication removably mounted on the frame, the reservoir having a dispensing nozzle and a closed opposite end;
(c) connector means attached to the dispensing nozzle for introducing the liquid medication into the patient;
(d) a displacement assembly including a rotation plate rotatably mounted on the frame and having a roller mounted on the plate in contact with and collapsing the reservoir to displace the liquid medication toward the dispensing nozzle, through the connector means and into the patient;
(e) motor means mounted on the rotation plate and associated with the frame to rotate the displacement assembly; and
(f) control means mounted on the rotation plate and operably associated with the motor means for controlling the operation of the displacement assembly.

* * * * *